United States Patent [19]
Ferro-Novick et al.

[11] Patent Number: 5,912,154
[45] Date of Patent: Jun. 15, 1999

[54] GERANYLGERANYL DIPHOSPHATE SYNTHASE PROTEINS, NUCLEIC ACID MOLECULES AND USES THEREOF

[75] Inventors: Susan Ferro-Novick, Guilford, Conn.; Yu Jiang, Princeton, N.J.

[73] Assignee: Yale University, New Haven, Conn.

[21] Appl. No.: 08/761,344

[22] Filed: Dec. 6, 1996

Related U.S. Application Data

[60] Provisional application No. 60/008,301, Dec. 7, 1995.

[51] Int. Cl.$^6$ .............................. C12N 9/10; C12N 15/54; C12N 15/70; C12N 15/81
[52] U.S. Cl. ...................... 435/193; 435/69.1; 435/69.7; 435/252.3; 435/254.21; 435/320.1; 536/23.2; 935/14; 935/28; 935/29; 935/69; 935/73
[58] Field of Search ................................ 435/69.1, 71.1, 435/131, 172.1, 193, 252.3, 300.1; 536/23.2, 23, 74

[56] References Cited

PUBLICATIONS

Brinkhaus et al., *Arch. Biochem Biophys.*, 266(2):607–612, Nov. 1988.
Chen et al., *Arch. Biochem Biophys.*, 314(2):399–404, Nov. 1994.
Chen et al., *Protein Sci.*, 3:600–607, 1994.
Chen et al., *J. Biol. Chem.*, 268(15):11002–11007, May 1993.
Math et al., *Proc. Natl. Acad. Sci. USA*, 89:6761–6764, Aug. 1992.
Ohnuma et al., *J. Biol. Chem.*, 269(20): 14792–14797, May 1994.
Sagami et al., *J. Biol. Chem.*, 269(32):20561–20566, Aug. 1994.
Sagami et al., *Acta Biochim. Polonica*, 41(3):293–302, 1994.
Caruttoli et al (1991) J. Biol. Chem. 266:5854–5859 "The Neurospora Crassa Carotenon Biosynthesis gene(Albino 3) reveals highly. . .".
Carle et al (1987) Meth Enz 155:468–483 "Orthogonal–Field–Alternation Gel Electrophoresis".
Viang et al (1995) J Biol Chem 270:21793–21799 "BTSI encodes a geranyl geranyl diphosphate synthase in saccaromyces cerevisige".
Jiang, Y., et al., Nature, vol. 366, "Bet2p and Mad2p are components of a prenyltransferase that adds geranylgeranyl onto Ypt1p and Sec4p", pp. 84–86, 1993.

*Primary Examiner*—Robert A. Wax
*Assistant Examiner*—William W. Moore
*Attorney, Agent, or Firm*—Sheridan Ross P.C.

[57] ABSTRACT

The present invention relates to yeast geranylgeranyl diphosphate synthase proteins and nucleic acid molecules encoding such proteins. Also included are methods to produce geranylgeranyl diphosphate and farnesyl diphosphate.

19 Claims, 7 Drawing Sheets

GERANYLGERANYL DIPHOSPHATE SYNTHASE PROTEINS, NUCLEIC ACID MOLECULES AND USES THEREOF

REFERENCE TO RELATED APPLICATION

This application claims priority from U.S. Provisional Application Ser. No. 60/008,301, filed Dec. 7, 1995, entitled "BTS1 Geranylgeranyl Diphosphate Synthase in *Saccharomyces Cerevisiae*".

REFERENCE TO GOVERNMENT SUPPORT

This invention was made in part with government support under CA46128, awarded by NCI, National Institutes of Health. The government has certain rights to this invention.

FIELD OF THE INVENTION

The present invention relates to yeast geranylgeranyl diphosphate synthase nucleic acid molecules and proteins encoded by such nucleic acid molecules. The present invention also includes methods to produce such nucleic acid molecules and proteins.

BACKGROUND OF THE INVENTION

Protein prenylation is a post-translational lipid modification that involves the covalent attachment of isoprenoid groups onto cysteine residues at or near the carboxyl termini of proteins. The attachment of a lipophilic isoprenoid group to proteins is believed to increase their hydrophobicity, allowing otherwise hydrophilic proteins to associate with membranes. Up to 0.5% of total cellular proteins are estimated to be prenylated. Known prenylated proteins include small GTP-binding proteins of the Ras superfamily, nuclear lamins, the yeast mating pheromone α-factor and trimeric G proteins. These proteins are engaged in a variety of cellular processes, which include the control of cell growth, signal transduction, cytokinesis, and intracellular membrane traffic.

Two different isoprenoid groups, farnesyl (15 carbons) and geranylgeranyl (20 carbons), are post-translationally attached to proteins. Farnesyl is added to proteins that terminate in a CAAX motif (where C is cysteine, A is an aliphatic amino acid, and X can be methionine, cysteine, alanine, glutamine, phenylalanine, or serine), while geranylgeranyl is transferred onto proteins that end in CAAL (where L is leucine), CC, or CXC motifs (X is any amino acid). Most known prenylated proteins are geranylgeranylated.

Farnesyl and geranylgeranyl groups are attached to proteins from all-trans farnesyl diphosphate (FPP) and all-trans geranylgeranyl diphosphate (GGPP), respectively. These lipid precursors are intermediates in the isoprenoid biosynthetic pathway. This pathway consists of a series of reactions by which mevalonate is converted into a diverse family of lipophilic molecules that contain a repetitive five-carbon structure. The isoprenoids are subsequently incorporated into a large number of end products, which includes: sterols, ubiquinones, dolichols, tRNAs, and prenylated proteins.

FPP is the product of the farnesyl diphosphate synthase reaction. This enzyme, which is the most abundant and widely occurring prenyltransferase, catalyzes the formation of FPP by the sequential addition of isopentenyl diphosphate (IPP) to dimethylallyl diphosphate (DMAPP), and geranyl diphosphate (GPP). In some organisms, GGPP is synthesized by a GGPP synthase (GGPPS) that catalyzes stepwise additions of IPP to DMAPP, GPP, and FPP. This type of GGPP synthase activity has been detected in mammalian tissue. However, eukaryotic geranylgeranyl diphosphate synthases are known that synthesize GGPP by the addition of a single molecule of IPP to FPP. But, due to its low activity and the problems in separating this enzyme from FPP synthase, its purification has proven to be difficult.

GGPP is the substrate for two different protein prenyltransferases, the type I (GGTase-I) and type II (GGTase-II) geranylgeranyl transferases. GGTase-I catalyzes the transfer of a geranylgeranyl group from GGPP onto proteins that terminate in a CAAL motif, while GGTase-II attaches geranylgeranyl to terminal CC or CXC residues. Its protein substrates include members of the Ras family of small GTP-binding proteins.

GGPP and FPP are important intermediates in the formation of a variety of derivatives which have important uses in the production of anti-cancer compounds, anti-tumor compounds, anti-cholesterol compounds and anti-ulcer compounds. For example, GGPP and FPP can be used in the prenylation of ras oncogene protein to inhibit neoplastic transformation. Taxol, a potent anti-cancer agent, is a GGPP derivative for which there is currently a lack of cost-effective, biosynthetic methods of production. Therefore, isolation of GGPP synthases for use in modulating GGPP and FPP biosynthetic pathways is both desirable and commercially valuable.

Although prior investigators have identified GGPP synthases in organisms such as bacteria, archaebacteria, rodents, bovines and filamentous fungi, GGPP synthases have been difficult to isolate. Prior to the present invention, a GGPP synthase has never been identified in yeast. Therefore, there is a need for the isolation of genes which encode eukaryotic GGPP synthases for use in the production of GGPP in large quantities, in a cost-effective manner.

SUMMARY OF THE INVENTION

The present invention relates to yeast geranylgeranyl diphosphate synthase nucleic acid molecules and proteins encoded by such nucleic acid molecules.

One embodiment of the present invention is an isolated nucleic acid molecule that encodes a yeast geranylgeranyl diphosphate synthase protein. A preferred embodiment of the present invention is an isolated nucleic acid molecule that encodes a Saccharomyces geranylgeranyl diphosphate synthase protein. A more preferred embodiment of the present invention is an isolated nucleic acid molecule that encodes a *Saccharomyces cerevisiae* geranylgeranyl diphosphate synthase protein. Other embodiments of the present invention include a recombinant molecule encoding a yeast geranylgeranyl diphosphate synthase protein, and a recombinant cell which is capable of expressing a nucleic acid molecule encoding a yeast geranylgeranyl diphosphate synthase protein.

Another embodiment of the present invention is an isolated protein comprising a yeast geranylgeranyl diphosphate synthase protein. Preferably, such a protein is a Saccharomyces geranylgeranyl diphosphate synthase protein, and more preferably, a *Saccharomyces cerevisiae* geranylgeranyl diphosphate synthase protein.

Yet another embodiment of the present invention is a method to produce geranylgeranyl diphosphate. Such a method includes culturing a recombinant cell which is capable of expressing a yeast geranylgeranyl diphosphate synthase protein.

Another embodiment of the present invention relates to a method to produce farnesyl diphosphate. Such a method includes culturing a recombinant cell with a reduced ability to express a yeast geranylgeranyl diphosphate synthase protein.

DETAILED DESCRIPTION OF THE INVENTION

Figure 1:
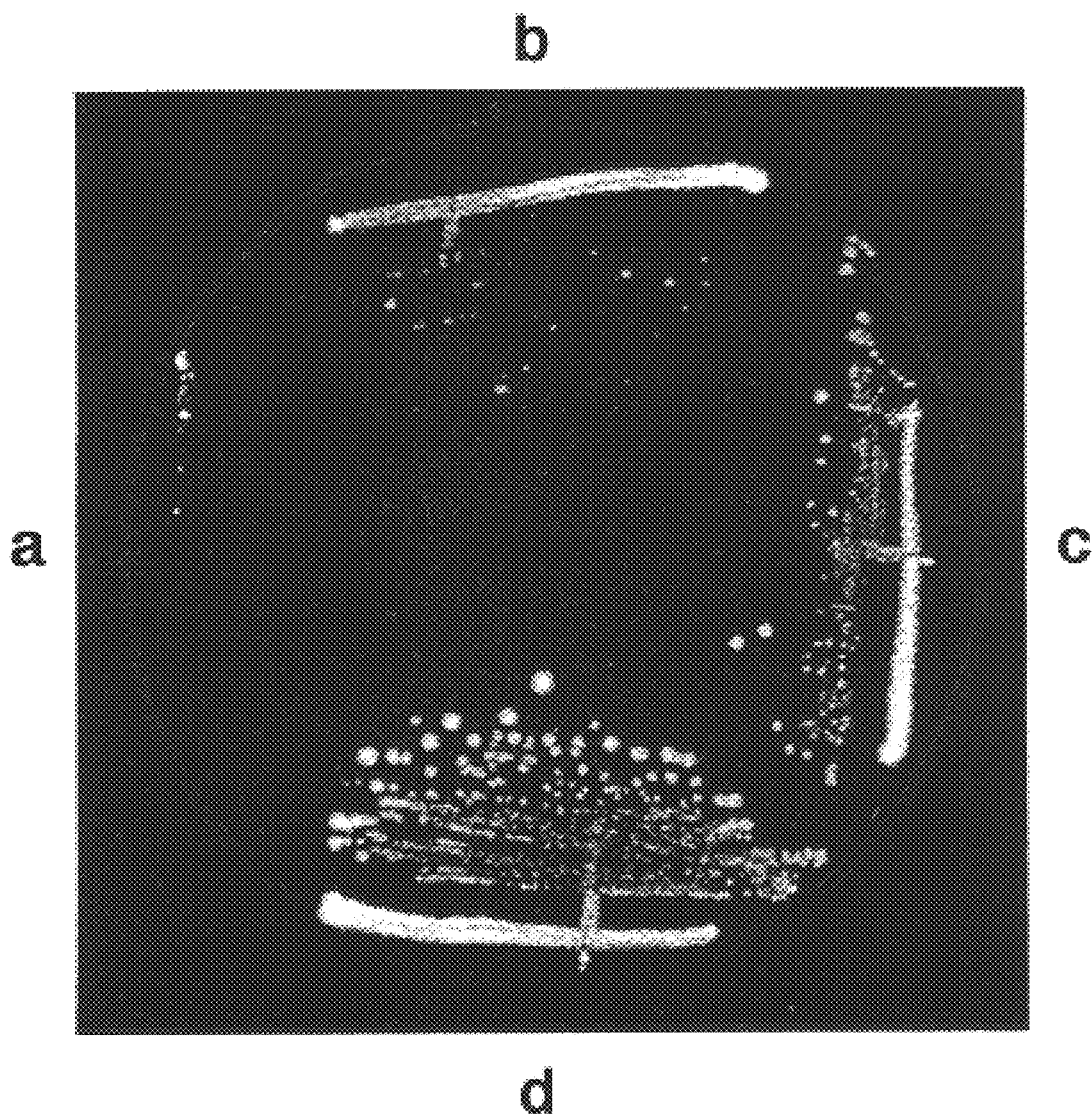
FIG. 1 shows that suppression of a GGTase-II mutant by a gene encoding a *Saccharomyces cerevisiae* geranylgeranyl diphosphate synthase is gene dosage dependent.

The present invention includes isolated geranylgeranyl diphosphate synthase (GGPP synthase) nucleic acid molecules and isolated geranylgeranyl diphosphate synthase proteins. Also included is the use of these proteins and nucleic acid molecules to produce geranylgeranyl diphosphate (GGPP).

One embodiment of the present invention is an isolated nucleic acid molecule that encodes a geranylgeranyl diphosphate synthase. Such a nucleic acid molecule can be an isolated nucleic acid molecule comprising a nucleic acid sequence encoding a yeast geranylgeranyl diphosphate synthase protein. While geranylgeranyl diphosphate synthase nucleic acid molecules and proteins have been previously identified in other organisms, prior to the present invention, none have been identified in yeast. Moreover, as described in more detail below, a yeast geranylgeranyl diphosphate synthase nucleic acid molecule and protein identified herein are significantly different than previously reported geranylgeranyl diphosphate synthase nucleic acid molecules and proteins from other organisms.

In another aspect of the present invention, such a nucleic acid molecule has a sequence that is greater than about 35% similar to the nucleic acid sequence of SEQ ID NO:1, which encodes a *Saccharomyces cerevisiae* GGPP synthase gene. Preferably, a nucleic acid molecule of the present invention has a sequence that is greater than about 50% similar to SEQ ID NO:1, more preferably greater than about 75% similar to SEQ ID NO:1, and even more preferably greater than about 90% similar to SEQ ID NO:1. In a further embodiment, a nucleic acid molecule of the present invention comprises the nucleic acid sequence of SEQ ID NO:1. The degree to which a nucleic acid molecule is similar to another nucleic acid molecule can be determined by standard methods known in the art. For example, several computerized data bases, such as NBLAST and EMBL/GenBank, allow comparisons of nucleic acid sequences and evaluations of the similarity between such sequences. Such data bases can directly compare such sequences and determine the percentage similarity between the sequences. Similarities (i.e., matching nucleic acid residues) between two sequences can be interspersed throughout the nucleic acid molecules or can be clustered (i.e., localized) in distinct regions on the nucleic acid molecules.

Comparison of a GGPP synthase nucleic acid molecule of the present invention with known GGPP synthase nucleic acid sequences reported in GenBank indicates that the coding region represented in SEQ ID NO:1 is most similar to that of GGPP synthase from the fungus, *Neurospora crassa*, being only about 31% similar to the *Neurospora crassa* GGPP synthase gene.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA. It is to be noted that the term "a" or "an" entity refers to one or more of that entity; for example, a gene refers to one or more genes or at least one gene. As such, the terms "a" (or "an"), "one or more" and "at least one" can be used interchangeably herein. It is also to be noted that the terms "comprising", "including", and "having" can be used interchangeably.

Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a GGPP synthase protein.

In another embodiment, an isolated nucleic acid molecule of the present invention hybridizes under stringent hybridization conditions with a *Saccharomyces cerevisiae* geranylgeranyl diphosphate synthase gene. In a preferred embodiment, such *Saccharomyces cerevisiae* geranylgeranyl diphosphate synthase gene comprises the nucleic acid sequence of SEQ ID NO:1. Preferably, such an isolated nucleic acid molecule of the present invention encodes a geranylgeranyl diphosphate synthase protein.

As used herein, stringent hybridization conditions refer to standard hybridization conditions under which nucleic acid molecules, including oligonucleotides, are used to identify molecules having similar nucleic acid sequences. Stringent hybridization conditions typically permit isolation of nucleic acid molecules having at least about 70% nucleic acid sequence identity with the nucleic acid molecule being used as a probe in the hybridization reaction. Such standard conditions are disclosed, for example, in Sambrook et al., 1989, *Molecular Cloning: A Laboratory Manual*, Cold Spring Harbor Labs Press. The reference Sambrook et al., ibid., is incorporated by reference herein in its entirety. Examples of such conditions include, but are not limited to, the following: Oligonucleotide probes of about 18–25 nucleotides in length with $T_m$'s ranging from about 50° C. to about 65° C., for example, can be hybridized to nucleic acid molecules typically immobilized on a filter (e.g., nitrocellulose filter) in a solution containing 5× SSPE, 1% Sarkosyl, 5× Denhardts and 0.1 mg/ml denatured salmon sperm DNA at 37° C. for about 2 to 12 hours. The filters are then washed 3 times in a wash solution containing 5× SSPE, 1% Sarkosyl at 37° C. for 15 minutes each. The filters can be further washed in a wash solution containing 2× SSPE, 1% Sarkosyl at 37° C. for 15 minutes per wash. Randomly primed DNA probes can be hybridized, for example, to nucleic acid molecules typically immobilized on a a filter (e.g., nitrocellulose filter) in a solution containing 5× SSPE, 1% Sarkosyl, 0.5% Blotto (dried milk in water), and 0.1 mg/ml denatured salmon sperm DNA at 42° C. for about 2 to 12 hours. The filters are then washed 2 times in a wash solution containing 5× SSPE, 1% Sarkosyl at 42° C. for 15 minutes each, followed by 2 washes in a wash solution containing 2× SSPE, 1% Sarkosyl at 42° C. for 15 minutes each.

As used herein, a GGPP synthase gene includes all nucleic acid sequences related to a natural GGPP synthase gene such as regulatory regions that control production of the GGPP synthase protein encoded by that gene (such as, but not limited to, transcription, translation or post-translation control regions) as well as the coding region itself. Similarly, a nucleic acid molecule of the present invention can include one or more regulatory regions, full-length or partial coding regions, or combinations thereof.

Reference herein to a nucleic acid sequence refers to the identified sequence as well as the complement of it. For example, nucleic acid sequence SEQ ID NO:1 represents the genomic DNA sequence of the coding strand of the nucleic acid molecule encoding GGPP synthase, the production of which is disclosed in the Examples. The complement of SEQ ID NO:1 refers to the nucleic acid sequence of the strand complementary to the strand having SEQ ID NO:1, which can easily be determined by those skilled in the art. The complement of SEQ ID NO:1 is represented herein as the nucleic acid sequence, SEQ ID NO:4. Likewise, a nucleic acid sequence complement of any nucleic acid sequence of the present invention refers to the nucleic acid sequence of the nucleic acid strand that is complementary to (i.e., can form a double helix with) the strand for which the sequence is cited. Therefore, a double-stranded nucleic acid molecule of the present invention for which one strand of such nucleic acid molecule is represented by SEQ ID NO:1, also comprises a complementary strand, SEQ ID NO:4, having a sequence that is a complement of that SEQ ID NO:1. As such, nucleic acid molecules of the present invention, which can be either double-stranded or single-stranded, include those nucleic acid molecules that form stable hybrids under stringent hybridization conditions with either a given sequence denoted herein and/or with the complement of that sequence. It should be noted that since nucleic acid sequencing technology is not entirely error-free, SEQ ID NO:1 (as well as other nucleic acid and protein sequences presented herein), at best, represents an apparent nucleic acid sequence of the nucleic acid molecule encoding a GGPP synthase protein of the present invention.

Reference herein to a nucleic acid molecule refers to the identified molecule as well as allelic variants thereof. As used herein, an allelic variant of a nucleic acid molecule is a nucleic acid molecule that occurs at essentially the same locus (or loci) in a genome as the identified molecule, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants further comprise variants based on the degeneracy of the genetic code. Therefore, any degenerate nucleic acid sequences that encode a GGPP synthase protein of the present invention are embodied herein. Allelic variants are well known to those skilled in the art and would be expected to be found within a given organism in which the genome is diploid and/or among a group of two or more organisms.

A GGPP synthase nucleic acid molecule of the present invention can be obtained from its natural source either as an entire (i.e., complete) nucleic acid molecule or a portion thereof. A GGPP synthase nucleic acid molecule can also be produced using recombinant DNA technology (e.g., polymerase chain reaction (PCR) amplification, cloning) or chemical synthesis.

Reference herein to a nucleic acid molecule refers to the identified molecule as well as homologues thereof. A nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., GGPP synthase activity or the ability to elicit an immune response against at least one epitope of a GGPP synthase protein) and/or by hybridization with a GGPP synthase gene.

The present invention also includes nucleic acid molecules that are oligonucleotides capable of hybridizing, under stringent hybridization conditions, with complementary regions of other, preferably longer, nucleic acid molecules of the present invention such as those comprising *Saccharomyces cerevisiae* GGPP synthase genes or other yeast GGPP synthase nucleic acid molecules. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit GGPP synthase protein production or activity. Such therapeutic applications include the use of such oligonucleotides in, for example, antisense-, triplex formation-, ribozyme- and/or RNA drug-based technologies. The present invention, therefore, includes such oligonucleotides and their use in a method of the present invention.

Knowing the nucleic acid sequences of certain *Saccharomyces cerevisiae* GGPP synthase nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain GGPP synthase nucleic acid molecules for other yeast species, particularly since, as described in detail in the Examples section, the isolation of *Saccharomyces cerevisiae* GGPP synthase nucleic acid molecules of the present invention is disclosed. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecules include yeast cDNA libraries as well as genomic DNA libraries. Similarly, preferred DNA sources to screen or from which to amplify nucleic acid molecules include yeast cDNA and genomic DNA. Techniques to clone and amplify genes are disclosed, for example, in Sambrook et al., ibid.

The present invention also includes nucleic acid molecules encoding a protein having at least a portion of SEQ ID NO:2 including nucleic acid molecules that have been modified to accommodate codon usage properties of the cells in which such nucleic acid molecules are to be expressed. As used herein, "a portion" of a given sequence can refer to a part or all of such sequence, within the size limitations for proteins and nucleic acid molecules encoded by such sequences as set forth in detail below.

As heretofore disclosed, isolated nucleic acid molecules of the present invention have the further characteristic of encoding an isolated protein comprising a GGPP synthase protein and preferably a yeast GGPP synthase protein. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis.

A further embodiment of the present invention is an isolated geranylgeranyl diphosphate synthase protein. Such a protein can be an isolated protein comprising a yeast geranylgeranyl diphosphate synthase protein. As noted above, while geranylgeranyl diphosphate synthase nucleic acid molecules and proteins have been previously identified in other organisms, prior to the present invention, none have been identified in yeast. A preferred yeast from which to isolate GGPP synthase proteins of the present invention (including isolation of the natural protein or production of the protein by recombinant or synthetic techniques) includes Saccharomyces. More preferably, a GGPP synthase protein of the present invention is isolated from *Saccharomyces cerevisiae*.

As previously discussed herein, a geranylgeranyl diphosphate synthase protein has the characteristic of catalyzing the stepwise additions of IPP to DMAPP, GPP and FPP to form GGPP. GGPP synthase can also catalyze the addition of a single molecule of IPP to FPP to form GGPP. Methods to identify a GGPP synthase protein of the present invention are further described in the Example section below.

In another aspect, a GGPP synthase protein of the present invention can include a protein comprising an amino acid sequence that is at least about 45%, preferably at least about 55%, and more preferably at least about 75%, and even more preferably at least about 90% similar to the amino acid sequence of SEQ ID NO:2, which is a *Saccharomyces cerevisiae* GGPP synthase amino acid sequence. The degree to which an amino acid sequence is similar to another amino acid sequence can be determined in the same manner as for nucleic acid sequences. For example, several computerized data bases, such as Swiss-Prot, allow direct comparisons of amino acid sequences and evaluations of the percentage similarity between such sequences.

A particularly preferred GGPP synthase protein of the present invention is a protein that comprises SEQ ID NO:2 (including, but not limited to the encoded protein, full-length proteins, processed proteins, fusion proteins and multivalent proteins) as well as a protein that is a truncated homologue of a protein that comprises SEQ ID NO:2. An even more preferred protein includes $PGGPPS_{335}$. Isolated proteins of the present invention can be produced in a variety of ways, including production and recovery of natural proteins, production and recovery of recombinant proteins, and chemical synthesis of the proteins. Examples of methods to produce such a protein are disclosed herein, including in the Examples section.

In a further embodiment, an isolated geranylgeranyl diphosphate synthase protein of the present invention is encoded by a nucleic acid molecule that hybridizes under stringent hybridization conditions with a *Saccharomyces cerevisiae* geranylgeranyl diphosphate synthase gene. Preferably, an isolated GGPP synthase protein of the present invention is encoded by a nucleic acid molecule that hybridizes under stringent hybridization conditions with a *Saccharomyces cerevisiae* GGPP synthase gene comprising the nucleic acid sequence of SEQ ID NO:1. More preferably, a GGPP synthase protein of the present invention includes a protein encoded by at least a portion of SEQ ID NO:1 and, as such, has an amino acid sequence that includes at least a portion of SEQ ID NO:2.

As used herein, a GGPP synthase protein can be a full-length protein or any homologue of such a protein. Examples of GGPP synthase homologues include GGPP synthase proteins in which amino acids have been deleted (e.g., a truncated version of the protein, such as a peptide), inserted, inverted, substituted and/or derivatized (e.g., by glycosylation, phosphorylation, acetylation, myristylation, prenylation, palmitoylation, amidation and/or addition of glycerophosphatidyl inositol) such that the homologue functions as a GGPP synthase and/or includes at least one epitope capable of eliciting an immune response against a GGPP synthase protein. That is, when the homologue is administered to an animal as an immunogen, using techniques known to those skilled in the art, the animal will produce a humoral and/or cellular immune response against at least one epitope of a GGPP synthase protein. The ability of a protein to effect an immune response, can be measured using techniques known to those skilled in the art.

GGPP synthase protein homologues can be the result of natural allelic variation or natural mutation. GGPP synthase protein homologues of the present invention can also be produced using techniques known in the art including, but not limited to, direct modifications to the protein or modifications to the gene encoding the protein using, for example, classic or recombinant DNA techniques to effect random or targeted mutagenesis.

The minimal size of a GGPP synthase homologue of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homologue is dependent on nucleic acid composition and percent similarity between the nucleic acid molecule and complementary sequence. It should also be noted that the extent of similarity required to form a stable hybrid can vary depending on whether the similar sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a GGPP synthase protein homologue of the present invention is from about 12 to about 18 nucleotides in length.

There is no limit, other than a practical limit, on the maximal size of such a nucleic acid molecule in that the nucleic acid molecule can include a portion of a gene, an entire gene, or multiple genes, or portions thereof. Similarly, the minimal size of a GGPP synthase protein homologue of the present invention is from about 4 to about 6 amino acids in length, with preferred sizes depending on whether a full-length, fusion, multivalent, or functional portions of such proteins are desired.

It is to be appreciated that the present invention also includes mimetopes of GGPP synthase proteins of the present invention that can be used in accordance with methods as disclosed for GGPP synthase proteins of the present invention. As used herein, a mimetope of a GGPP synthase protein of the present invention refers to any compound that is able to mimic the activity of such a GGPP synthase protein, often because the mimetope has a structure that mimics the GGPP synthase protein. Mimetopes can be, but are not limited to, peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of the isolated protein of the present invention is a fusion protein that includes a GGPP synthase protein-containing domain attached to a fusion segment. Inclusion of a fusion segment as part of a GGPP synthase protein of the present invention can enhance the protein's stability during production, storage and/or use. Furthermore, a fusion segment can function as a tool to simplify purification of a GGPP synthase protein, such as to enable purification of the resultant fusion protein using affinity chromatography. A suitable fusion segment can be a domain of any size that has the desired function (e.g., imparts increased stability and/or simplifies purification of a protein). It is within the scope of the present invention to use one or more fusion segments. Fusion segments can be joined to amino and/or carboxyl termini of the GGPP synthase-containing domain of the protein. Linkages between fusion segments and GGPP synthase-containing domains of fusion proteins can be susceptible to cleavage in order to enable straight-forward recovery of the GGPP synthase-containing domains of such proteins. Fusion proteins are preferably produced by culturing a recombinant cell transformed with a nucleic acid molecule that encodes a protein including the fusion segment attached to either the carboxyl and/or amino terminal end of a GGPP synthase-containing domain.

Preferred fusion segments for use in the present invention include a metal binding domain (e.g., a poly-histidine segment capable of binding to a divalent metal ion); an immunoglobulin binding domain (e.g., Protein A, Protein G, B cell, Fc receptor or complement protein antibody-binding domains); a sugar binding domain (e.g., a maltose binding domain from a maltose binding protein); a glutathione binding domain; and/or a "tag" domain (e.g., at least a portion of β-galactosidase, a strep tag peptide, other domains that can be purified using compounds that bind to the domain, such as monoclonal antibodies). More preferred fusion segments include glutathione-S-transferase and a poly-histidine segment. A particularly preferred fusion segment of the present invention is a poly-histidine segment.

Translation of SEQ ID NO:1 suggests that nucleic acid molecule nGGPPS$_{1005}$ encodes a full-length GGPP synthase protein of about 335 amino acids, referred to herein as PGGPPS$_{335}$. nGGPPS$_{1005}$ represents the open reading frame, excluding the termination (stop) codon, corresponding to a genomic nucleic acid sequence comprising nucleic acid molecule nGGPPS$_{1600}$ of the present invention, the nucleic acid sequence of which is represented herein by SEQ ID NO:3. As such, the open reading frame within SEQ ID NO:3 has an initiation (start) codon spanning from about nucleotide 301 through about nucleotide 303 of SEQ ID NO:3 and a termination codon spanning from about nucleotide 1306 through about nucleotide 1308 of SEQ ID NO:3. The complement of SEQ ID NO:3 refers to the nucleic acid sequence of the strand complementary to the strand having SEQ ID NO:3, and is represented herein as SEQ ID NO:5.

The deduced amino acid sequence of PGGPPS$_{335}$ is represented herein as SEQ ID NO:2. Based on that amino acid sequence, PGGPPS$_{335}$ has an estimated molecular weight of about 38,627 daltons. The amino acid sequence of PGGPPS$_{335}$ is predicted to be hydrophilic overall, with no significant hydrophobic stretches.

One embodiment of the present invention includes a recombinant molecule comprising a nucleic acid molecule encoding a GGPP synthase protein of the present invention. A recombinant molecule, also referred to as a recombinant vector, of the present invention includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant molecules can be used in the cloning, sequencing, and/or otherwise manipulating of GGPP synthase nucleic acid molecules of the present invention. A recombinant molecule of the present invention can be used in the expression of nucleic acid molecules of the present invention. Preferred recombinant vectors are capable of replicating in a transformed cell.

Suitable and preferred nucleic acid molecules to include in recombinant molecules of the present invention are as disclosed herein for suitable and preferred GGPP synthase nucleic acid molecules per se. A particularly preferred nucleic acid molecule to include in recombinant molecules, and particularly in recombinant molecules of the present invention includes nGGPPS$_{1005}$.

Included in the present invention is a recombinant cell capable of expressing a nucleic acid molecule of the present invention. A recombinant cell of the present invention includes suitable host cells to transform with a nucleic acid molecule of the present invention. Host cells can be either untransformed cells or cells that are already transformed with at least one nucleic acid molecule. Host cells of the present invention either can be endogenously (i.e., naturally) capable of producing GGPP synthase proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), insect, and other animal and plant cells. Preferred host cells include yeast cells and bacterial cells. More preferred host cells include cells from Saccharomyces and cells from Escherichia. A particularly preferred host cell is *Saccharomyces cerevisiae*. Another particularly preferred host cell is *Escherichia coli*.

A recombinant cell is preferably produced by transforming a host cell with one or more recombinant molecules. A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed. Details regarding the production of a *Saccharomyces cerevisiae* GGPP synthase nucleic acid molecule-containing recombinant molecule are disclosed in the Examples section herein. The phrase operatively linked refers to insertion of a nucleic acid molecule into an expression vector in a manner such that the molecule is able to be expressed when transformed into a host cell.

As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal (including yeast), insect, other animal, and plant cells. Preferred expression vectors of the present invention can direct gene expression in yeast cells and more preferably in the specific cell types heretofore disclosed.

Transformation of a recombinant molecule into a cell can be accomplished by any method by which a recombinant molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable and preferred nucleic acid molecules with which to transform a cell are as disclosed herein for suitable and preferred GGPP synthase nucleic acid molecules per se. Particularly preferred nucleic acid molecules to include in recombinant cells of the present invention include $nGGPPS_{1005}$.

Recombinant molecules of the present invention may also (a) contain secretory signals (i.e., signal segment nucleic acid sequences) to enable an expressed GGPP synthase protein of the present invention to be secreted from the cell that produces the protein and/or (b) contain fusion sequences which lead to the expression of nucleic acid molecules of the present invention as fusion proteins. Examples of suitable signal segments and fusion segments encoded by fusion segment nucleic acids are disclosed herein. Eukaryotic recombinant molecules may include intervening and/or untranslated sequences surrounding and/or within the nucleic acid sequences of nucleic acid molecules of the present invention. Suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (λ) (such as $\lambda P_L$ and $\lambda P_R$ and fusions that include such promoters), bacteriophage T7, T7lac, bacteriophage T3, bacteriophage SP6, bacteriophage SP01, metallothionein, α-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters, simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Most preferred transcription control sequences include those which function in yeast and include, but are not limited to various galactose promoters or combinations such as GAL1, Gal7, Gal10, and GAP/GAL (GAP: glyceraldehyde-3-phosphate dehydrogenase). Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a yeast, such as a *Saccharomyces cerevisiae* molecule prior to isolation.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

In accordance with the present invention, recombinant cells of the present invention can be used to produce one or more proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a GGPP synthase protein of the present invention. Such a medium is typically an aqueous medium comprising assimilable carbon, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell membrane.

The phrase "recovering the protein" can refer simply to collecting the whole fermentation medium containing the protein and need not imply additional steps of separation or purification. Proteins of the present invention can be further purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Another embodiment of the present invention relates to a method to produce geranylgeranyl diphosphate (GGPP). As described above, GGPP is the source of geranylgeranyl groups which are used to prenylate proteins in the isoprenoid biosynthetic pathway. GGPP is an important intermediate in the formation of a variety of derivatives which have important uses in the production of anti-cancer compounds, anti-tumor compounds, anti-cholesterol compounds and anti-ulcer compounds.

Such a method to produce GGPP includes culturing a recombinant cell such that GGPP is produced, wherein such cell comprises an isolated nucleic acid molecule encoding a geranylgeranyl diphosphate synthase of the present invention. Such a recombinant cell can include bacterial, fungal (including yeast), insect or other animal and plant cells. Preferred recombinant cells include yeast cells and bacterial cells. More preferred recombinant cells include yeast of the genus Saccharomyces and bacteria of the genus Escherichia. A particularly preferred recombinant cell is *Saccharomyces cerevisiae*. Another particularly preferred host cell is *Escherichia coli*.

Another embodiment of the present invention relates to a method to produce farnesyl diphosphate (FPP) comprising culturing a recombinant cell which has a reduced ability to produce geranylgeranyl diphosphate synthase such that farnesyl diphosphate is produced. As previously discussed herein, FPP, like GGPP, is a precursor in the isoprenoid biosynthetic pathway. Formation of GGPP can be catalyzed by stepwise additions of IPP to DMAPP, GPP and FPP, or in eukaryotes, by addition of a single molecule of IPP to FPP. Therefore, since production of FPP precedes production of GGPP in the biosynthetic pathway, reduction of production of a GGPP synthase of the present invention can be useful to enhance the production of FPP. Most preferably, a recombinant cell which has a reduced ability to produce a geranylgeranyl diphosphate synthase of the present invention contains an endogenous nucleic acid molecule encoding a GGPP synthase of the present invention which has been modified such that GGPP synthase production is reduced. Such a modification can include a mutation in the GGPP synthase nucleic acid sequence of the present invention, such mutation resulting in expression of a GGPP synthase protein having reduced enzymatic activity. Reduction of GGPP synthase enzymatic activity can result in reduced production of GGPP and in accumulation of FPP within the recombinant cell. Such a mutation in a GGPP synthase nucleic acid sequence can be in any portion of the GGPP synthase gene, such as in the regulatory regions that control production of the GGPP synthase protein encoded by that gene (such as, but not limited to, transcription, translation or post-translation control regions) as well as the coding region itself.

Alternatively, a recombinant cell which has a reduced ability to produce a geranylgeranyl diphosphate synthase of the present invention does not contain an endogenous nucleic acid molecule encoding a GGPP synthase of the present invention, but does contain recombinant nucleic acid molecules encoding portions of the GGPP synthetic pathway, including a GGPP synthase of the present invention which has been modified such that GGPP synthase production is reduced. Such modifications have been discussed previously herein. Such reduction in GGPP synthase thereby decreases the production of GGPP and increases, or enhances, production or accumulation of FPP.

A GGPP synthase nucleic acid molecule with reduced ability to produce GGPP synthase protein can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecules with reduced ability to produce GGPP can be selected from a mixture of modified nucleic acids by screening for the function of the protein encoded by the nucleic acid (e.g., ability to convert FPP to GGPP) and/or by hybridization with an isolated GGPP synthase gene of the present invention. Such a cell containing a modified recombinant GGPP synthase gene is exemplified in Example 4.

The following examples are provided for the purposes of illustration and are not intended to limit the scope of the present invention.

The following strains were used in Examples 1–8 below: ANY119 (MATα, bet2-1, ura3-52, his4-619), NY648 (MAT a/α, leu2-3, 112/leu2-3, 112, ura3-52/ura3-52), NY180 (MATα, ura3-52, leu2-3, 112), SFNY26-6A (MATα, his4-619), and SFNY368 (MATα, ura3-52, leu2-3, 112, URA3::BTS1). Yeast strains were grown at 25° C. or 37° C. in either YP or selective minimal medium that was supplemented with 2% glucose.

EXAMPLE 1

The following example demonstrates the isolation of a plasmid (pSJ28) which is a suppressor of the bet-2-1 mutant bet-2-1.

GGTase-II is composed of three subunits (BET2, BET4, and MRS6). Bet2p, the β-subunit of this enzyme complex, forms a complex with Bet4p, the α-subunit. Mrs6p is an escort protein that presents protein substrate to the Bet2p-Bet4p complex. During geranylgeranylation, the Bet2p-Bet4p complex binds to and transfers GGPP to Ypt1p, Sec4p, and other small GTP-binding proteins. bet2-1 is a temperature-sensitive mutant for the *Saccharomyces cerevisiae* β-subunit of GGTase-II. The mutant grows at 25° C. (permissive temperature) but dies at 37° C. To isolate genes whose products may interact with the Bet2 protein (Bet2p), a yeast genomic library was prepared by ligation of genomic DNA that was prepared from the bet2-1 mutant (ANY119). This DNA was partially digested with Sau3A and inserted into the BamHI site of pRS316 (CEN, URA3). The library was used to transform ANY119, and the transformants (1×10$^5$) were selected on minimal medium lacking uracil. After a 3-day incubation at 25° C., the cells were stamped onto YPD plates and incubated overnight at 37° C. 11 positive transformants were obtained. Plasmids (pS1-pS11) retrieved from these transformants were amplified in *Escherichia coli* and retested in ANY119.

The growth of mutant cells containing six of these plasmids (group A) was indistinguishable from that of wild type at 37° C. (data not shown). The other five (group B), however, did not suppress as well. Restriction analysis indicated that the plasmids in group A contained the BET2 structural gene. Since the genomic library was prepared from bet2-1 mutant cells, the restoration of growth observed at 37° C. is not true complementation. Plasmids in group B contained an overlapping 2.0-kb region of DNA. Therefore, the gene that suppresses the bet2-1 mutant is located within this 2.0-kb fragment.

The smallest group B plasmid (pS8) that was isolated contained a 2.8-kb insert (FIG. 1b). To analyze the ability of this insert to suppress bet2-1, this fragment was cloned into a high copy URA3 vector (pRS426) to generate the plasmid, pSJ28. When pSJ28 was transformed into bet2-1 mutant cells, suppression was significantly enhanced (FIG. 1, compare b and c to the mutant alone in a). In fact, growth of the mutant was restored to that of wild type (FIG. 1, compare c and d), suggesting that suppression was gene dosage dependent.

As demonstrated in this example, in an attempt to identify new genes whose products may interact with Bet2p, the present inventors isolated a suppressor of the bet2-1 mutant. The examples below demonstrate that this suppressor gene, called BTS1, encodes a geranylgeranyl diphosphate synthase, an previously unidentified prenyltransferase of the yeast isoprenoid biosynthetic pathway. The BTS1 gene product functions on this pathway to convert FPP to GGPP.

EXAMPLE 2

The following example demonstrates that plasmid pSJ28 increases the membrane-bound pool of two GGPP-dependent proteins in bet2-1 mutant cells.

Figure 2:
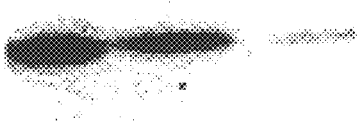
FIG. 2 shows that overexpression of a *Saccharomyces cerevisiae* geranylgeranyl diphosphate synthase gene increases the membrane-bound pool of two GGPP-dependent membrane proteins.
Figure 2:
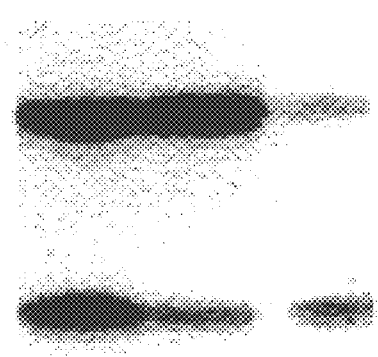
Figure 2:
Figure 2:
Figure 2:
Figure 2:

The membrane association of Ypt1p and Sec4p, two small GTP-binding proteins that regulate intracellular membrane traffic, is defective in bet2 mutant cells. This defect is a consequence of the failure to geranylgeranylate these proteins. Thus, the lethal phenotype of the bet2-1 mutant is likely to be a consequence of the inability of these proteins to attach to membranes. Since plasmid pSJ28 suppresses the growth defect of the bet2-1 mutant at 37° C., the present inventors believed it would also cure the membrane attachment defect observed in these cells. To address this possibility, pSJ28 was transformed into bet2-1. When the distribution of Ypt1p and Sec4p was examined in these transformants and compared to the mutant and wild type, pSJ28 was found to enhance the membrane association of these small GTP-binding proteins (FIG. 2, compare the amount in the lysate (T) to the supernatant (S) and pellet (P) fractions). The presence of pSJ28 did not lead to an increase in the residual GGTase-II activity that can be measured in bet2 mutant cells. Thus, the restoration of the membrane association of Ypt1p and Sec4p is not a consequence of increasing GGTase-II activity.

EXAMPLE 3

The following example illustrates the cloning and sequencing of the bet2-1 suppressor gene.

Figure 3:
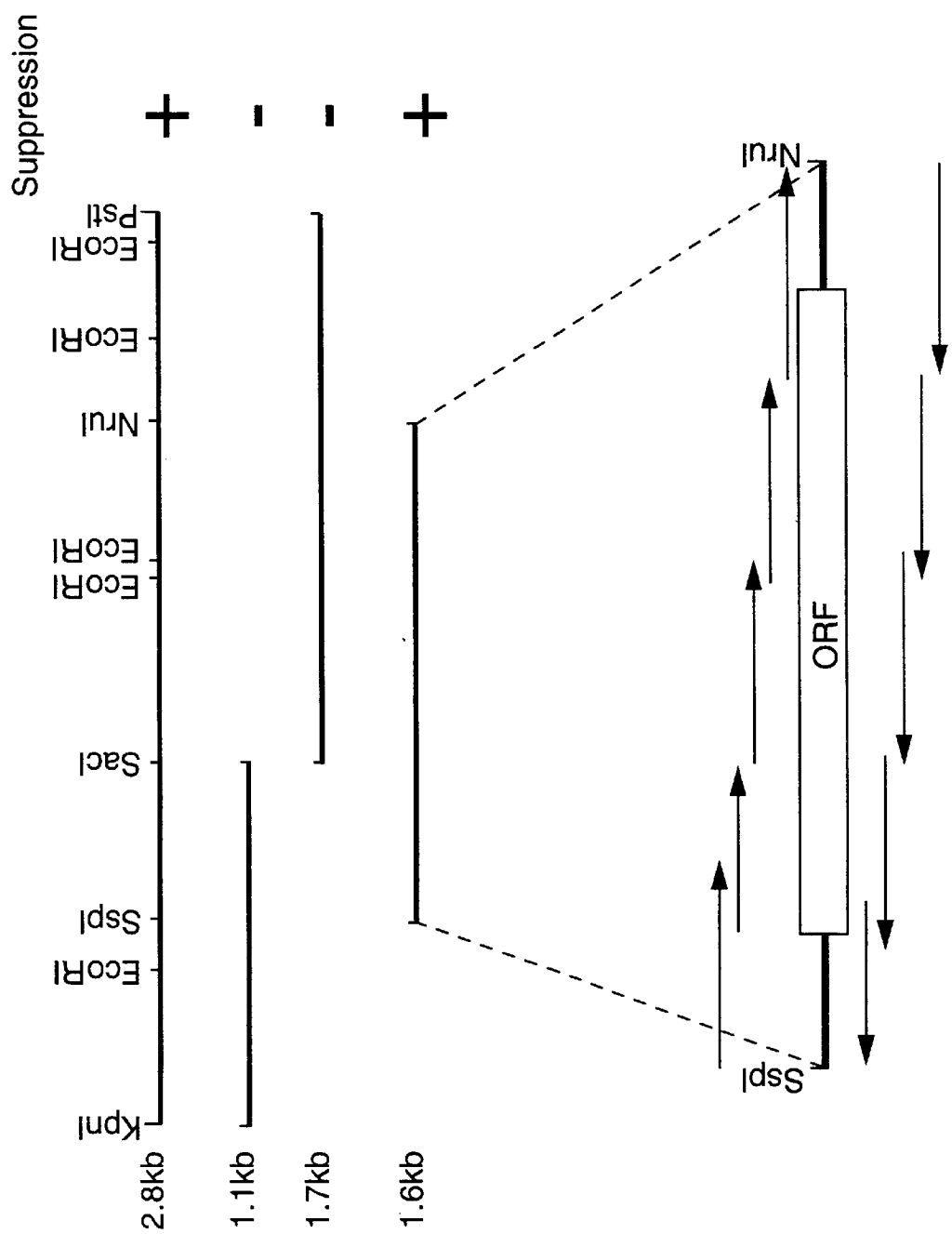
FIG. 3 schematically illustrates the strategy for sequencing an isolated *Saccharomyces cerevisiae* geranylgeranyl diphosphate synthase nucleic acid molecule of the present invention.

To localize the nucleic acid molecule encoding the suppressor within the 2.8-kb genomic fragment described above, subclones of pSJ28 were constructed and inserted into pRS316 (URA3, CEN). Suppression studies revealed that the SacI site contained within this fragment is critical for its activity. The smallest region of DNA capable of suppressing bet2-1 was found to be an approximately 1.6-kb SspI-NruII fragment, referred to herein as nGGPPS$_{1600}$ (SEQ ID NO:3). This region of DNA was sequenced in both directions using the strategy shown in FIG. 3. The DNA sequence of the BTS1 gene was determined by the dideoxynucleotide chain termination method. The reactions were performed using the Sequenase (U.S. Biochemical Corp.) protocol, and the data were analyzed with GCG software. Homology searches were performed with the EMBO/GenBank and Swiss-Prot data bases. An open reading frame of 1005 base pairs that spans the SacI site was identified. The nucleic acid molecule that encodes this open reading frame is referred to as BTS1 (Bet Two Suppressor), or nGG-PPS$_{1005}$ (SEQ ID NO:1). The BTS1 product, also referred to herein as Bts1p, or PGGPPS$_{335}$ (SEQ ID NO:2), was predicted to encode a protein of 335 amino acids with a calculated molecular mass of 38,627 daltons. Overall, the amino acid composition of Bts1p is hydrophilic, and no significant hydrophobic stretches were observed.

Comparison of the predicted Bts1p amino acid sequence with the Swiss-Prot protein sequence data base revealed that Bts1p and the *N. crassa* albino-3 gene product identified previously (Carattoli et al., *J. Biol. Chem.*, 1991, Vol. 266:5854–5859) are 40% identical at the amino acid level with the most conserved region localized to the middle of these proteins. The albino-3 gene encodes a geranylgeranyl diphosphate synthase in the carotenoid biosynthetic pathway of *N. crassa*. Bts1p also contains five conserved regions found in other FPP and GGPP synthases, including the aspartate-rich sequences proposed to be involved in binding and catalysis. These comparisons indicated that BTS1 encodes a previously unidentified GGPP synthase, a prenyltransferase of *S. cerevisiae*.

EXAMPLE 4

The following example demonstrates that the BTS1, or nGGPPS$_{1005}$, nucleic acid molecule is not essential for vegetative growth of yeast cells, but in its absence, growth is impaired.

To investigate if BTS1 is required for the vegetative growth of yeast cells, one copy of this gene was disrupted in diploid cells and tetrad analysis was performed.

To disrupt BTS1, a 1.7-kb DraI-NruI fragment containing the BTS1 gene was excised from pS8 and cloned into the PvuII site of pUC118 to generate pSJ30. The plasmid-borne disruption of BTS1 was constructed by replacing a 0.65-kb SacI-EcoRI fragment in pSJ30 with a 1.2-kb SacI-EcoRI fragment containing the URA3 gene. The resulting plasmid (pSJ31) was digested with SspI and BglII and transformed into NY648. The transformants were sporulated, and tetrad analysis was performed.

After 3 days at 25° C., in all of the 48 tetrads examined, four viable spores were obtained. However, two of the colonies in each of the tetrads displayed a growth defect at 25° C. The large colonies were Ura$^-$ and the small colonies were Ura$^+$, indicating that they contained the disrupted BTS1 gene.

To confirm that the small colonies contained the disrupted BTS1 nucleic acid molecule, yeast genomic DNA prepared from NTY180 (above) or SFNY368 (below) was examined by DNA-DNA hybridization. Genomic DNA digested with BglII was fractionated on a 0.8% agarose gel and transferred to a BioTrans membrane (ICN). The blot was probed with a radiolabeled 0.65-kb SacI-EcoRI fragment, containing BST1, prepared by random-primer labeling and visualized by autoradiography.

Figure 4:
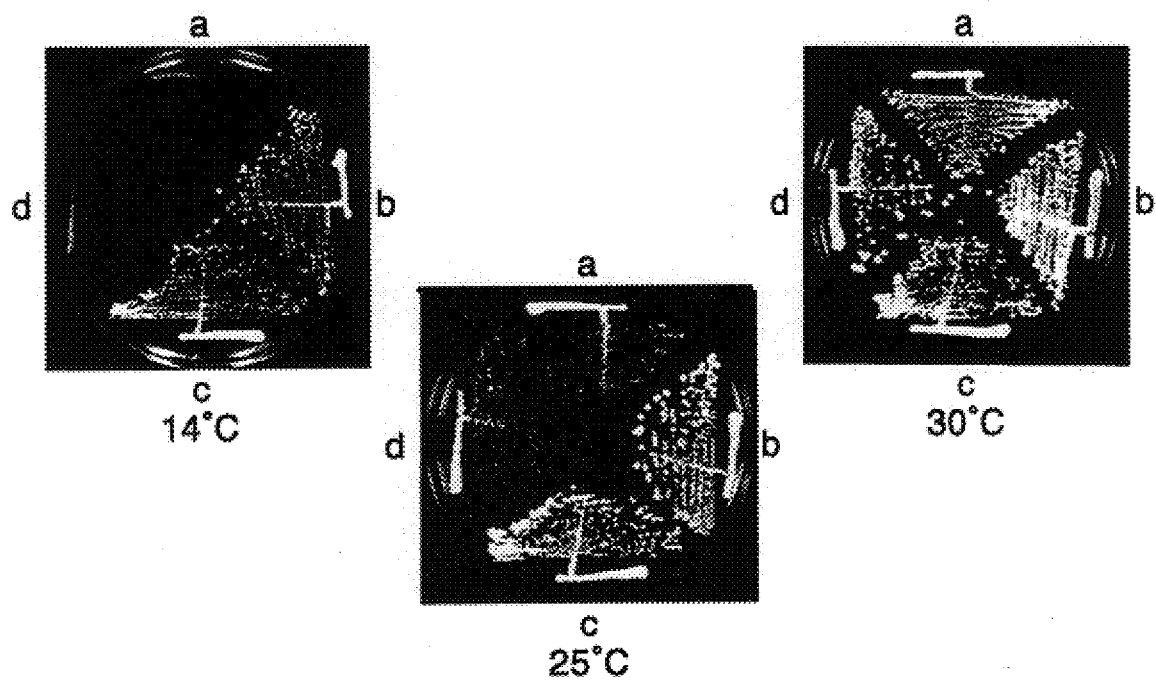
FIG. 4 shows that a diploid yeast cell containing one copy of a disrupted GGPP synthase gene is cold-sensitive for growth.

The above results demonstrate that BTS1 is not essential for the vegetative growth of yeast cells, but that in its absence, growth is impaired. The growth of the disrupted strain (SFNY368 or ΔBTS1) was examined further at different temperatures. As shown in FIG. 4, ΔBTS1 cells (FIGS. 4, *a* and *d*) grew as well as wild type at 30° C. (FIGS. 4, *b* and *c*). However, at lower temperatures (25° C. and 14° C.) a growth defect emerged. Only small colonies appeared after 3 days at 25° C. (FIGS. 4, *a* and *d*), while at 14° C., the cells did not survive (FIGS. 4, *a* and *d*). This result clearly demonstrated that SFNY368 is cold sensitive for growth.

Because each of the subunits of the GGTase-II are essential, it would be expected that BTS1 would also be required for the vegetative growth of yeast cells. Surprisingly, the ΔBTS1 strain was only cold sensitive for growth. Furthermore, the growth of this strain was not impaired at 30° C. or higher temperatures. When the membrane association of Ypt1p and Sec4p was examined in ΔBTS1 cells grown at 30° C., a small fraction of each of these proteins was membrane bound. Thus, BTS1-depleted cells are able to prenylate proteins at a level that is sufficient to sustain cell growth at higher temperatures. When these cells were shifted to 14° C., less membrane-bound Ypt1p and Sec4p was detected, implying that growth ceases as a consequence of the failure to prenylate these essential proteins.

EXAMPLE 5

The following example shows that the BTS1 gene product is required for the membrane attachment of Ypt1p and Sec4p.

Ypt1p and Sec4p are two small GTP-binding proteins that regulate intracellular membrane traffic. Like many small GTP-binding proteins, they are synthesized in the cytosol but become membrane-bound to perform their function. The ability of Ypt1p and Sec4p to bind to membranes is conferred by the addition of the 20-carbon, geranylgeranyl moiety. The geranylgeranylation of these proteins is catalyzed by a protein prenyltransferase that utilizes GGPP as a lipid donor. If BTS1 encodes a GGPP synthase, disruption of this gene should result in the depletion of GGPP. Consequently, the geranylgeranylation of Ypt1p and Sec4p will be abolished.

To test this hypothesis, the membrane association of these proteins in the ΔBTS1 strain, SFNY368, was examined. SFNY368 was grown at 30° C. for 12 h until the A$_{600}$ was 1.0 prior to shifting the cells to 14° C. for another 12 h. Aliquots of cells were removed at each time point, converted to spheroplasts, lysed, and centrifuged at 450×g to remove unbroken cells and nuclei. Subsequently, these lysates were centrifuged at 100,000×g for 1 h to obtain supernatant and pellet fractions, and the distribution of Ypt1p and Sec4p was examined in each of these fractions by Western blot analysis.

Wild type (NY180) and the ΔBTS1 strain (SFNY368) were grown overnight at 30° C. in YPD medium to early exponential phase. 1 aliquot of cells (150 A$_{599}$ units) was pelleted and washed once with ice-cold 10 mM sodium azide. The remaining cells were shifted to 14° C., and the incubation was continued for 12 h before the cells were harvested. To generate spheroplasts, cells were resuspended in 0.7 ml of 10 mM ice-cold sodium azide and mixed with an equal volume of 2×spheroplast medium (2.8M sorbitol, 100 mM Tris-HCl (pH 7.5), 20 mM sodium azide) containing 100 units of zymolyase. After a 1-h incubation at 25° C., the spheroplasts were harvested by centrifugation in a clinical centrifuge during a spin at 1400 rpm for 5 min, washed, and lysed in 1.4 ml of ice-cold lysis buffer (0.8M sorbitol, 10 mM triethanolamine (pH 7.2), 1 mM EDTA). Cell debris was removed during a 3-min spin at 450×g, and the supernatant from this spin was centrifuged at 100,000×g for 1 h to generate a soluble fraction. The pellet was resuspended in a volume of lysis buffer equal to the supernatant. Samples were electrophoresed and subjected to Western blot analysis using anti-Ypt1p or anti-Sec4p antibodies (1:2000 dilution).

Figure 5A:
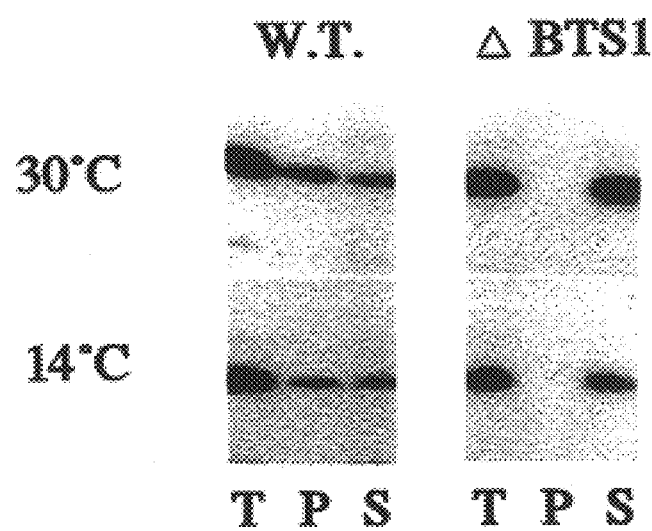
FIG. 5 is a Western blot showing that membrane attachment of small GTP-binding proteins, Sec4p and Ypt1p, is defective in a yeast cell containing one copy of a disrupted GGPP synthase gene.
Figure 5B:
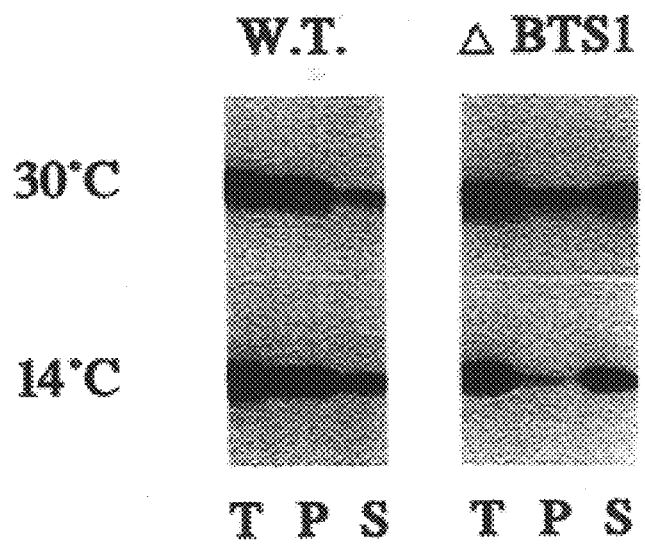

In wild type cells (FIG. 5, compare the amount in the lysate (T) to the supernatant (S) and pellet (P)), most of Ypt1p (FIG. 5A) and Sec4p (FIG. 5B) was membrane-bound at both time points, and the change in temperature did not affect their membrane association (FIG. 5, compare 14° C. and 30° C.). However, in SFNY368, most of the Ypt1p and Sec4p was soluble at both temperatures (FIG. 5, compare the amount in the lysate (T) to the supernatant (S) and pellet (P)), although this defect was more pronounced at 14° C. Thus, the membrane association of these small GTP-binding proteins is defective in ΔBTS1 cells, demonstrating that BTS1 encodes a GGPP synthase.

EXAMPLE 6

The following example further demonstrates that BTS1 encodes a geranylgeranyl diphosphate synthase.

To demonstrate that BTS1 encodes a geranylgeranyl diphosphate synthase, the gene was cloned into a pUC118 vector to express it in *E. coli*. The BTS1 open reading frame sequence was generated by polymerase chain reaction using two primers that overlapped the initiation codon or the region 100 base pairs downstream from the stop codon.

EcoRI and ClaI sites were also incorporated into the 5'- and 3'-ends, respectively. The polymerase chain reaction product was digested with EcoRI and ClaI and cloned into the pUC118 expression vector. The resulting gene fusion encodes a Bts1 protein with six additional $NH_2$-terminal amino acids from β-galactosidase. This construct was then transformed into JM101 bacterial cells and expressed.

Crude extracts of *E. coli* containing pUC118 (control) or pUC118/BTS1 were assayed for prenyltransferase activity in the presence of [1-$^{14}$C]IPP, using DMAPP or FPP as the allylic substrate, and the reaction mixture was analyzed by HPLC. The standard assay mixture contained 20 mM BHDA buffer (pH 7.0), 10 mM β-mercaptoethanol, 1 mM $MgCl_2$, 0.1% (w/v) bovine serum albumin, 200 μm DMAPP or FPP, 20 μM [1-$^{14}$C]IPP (10 μCi/μmol purchased from Amersham), and 70–80 μg of protein in a total volume of 200 μl. DMAPP, FPP, and GGPP were synthesized. After 10 min at 37° C., 200 μl of $CH_3OH$—HCl (4:1) was added, and the incubation was continued for 30 min. The reaction mixture was extracted with 1 ml of ligroin, and 0.5 ml of the ligroin layer was mixed with 10 ml of Cytoscint-ES (ICN) for the measurement of radioactivity in a Packard TriCarb 4530 liquid scintillation spectrometer. Products were analyzed using HPLC. For the product analysis, bovine serum albumin was omitted from the standard assay mixture, but 10 mM sodium fluoride was present to suppress phosphatase activity. After a 1-h incubation at 37° C., the reaction was terminated by the addition of EDTA (12.5 mM, final concentration). Unlabeled GGPP (25 μg.) was added, and 150 μl of the mixture was injected onto a Shodex Asahipak ODP-50 column (4.6 mm (inner diameter)×250 mm). 2-min fractions were collected, and the radioactivity in each fraction was determined by liquid scintillation counter after the addition of 15 ml of Cytoscint-ES.

Figure 6:
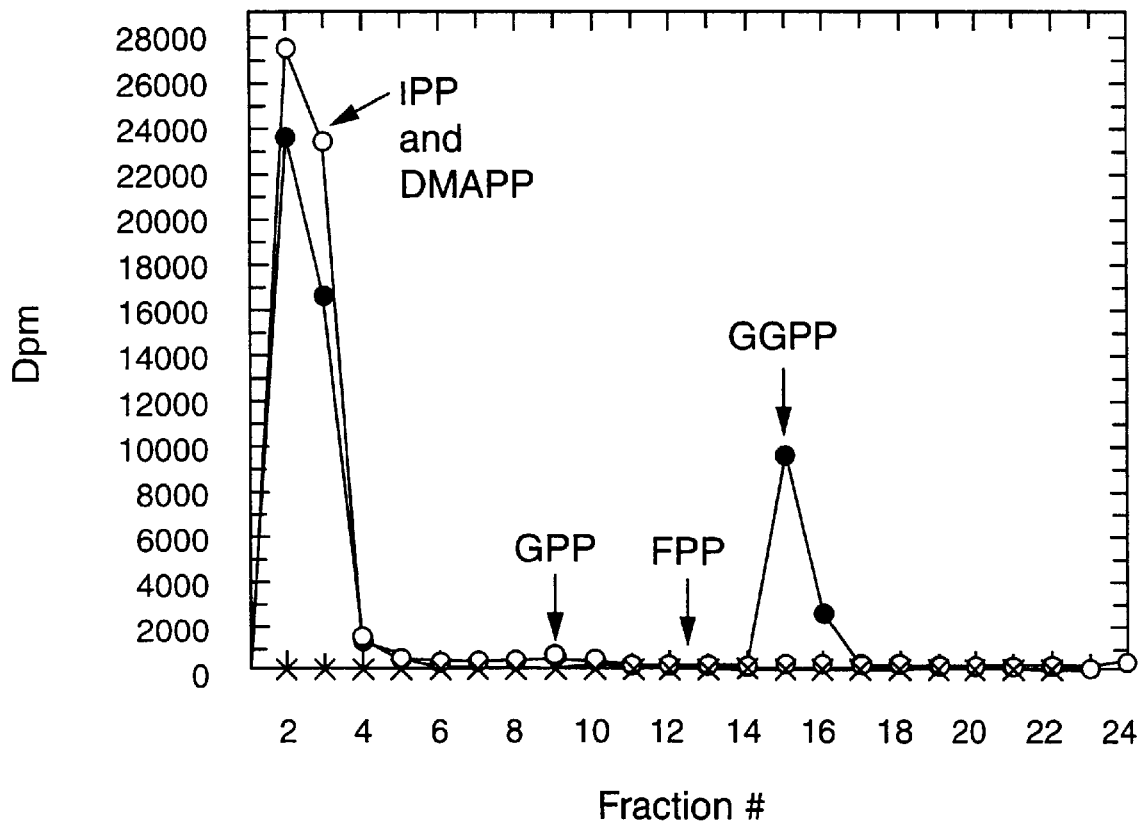
FIG. 6 is a reverse-phase HPLC elution profile of radio-labeled prenyltransferase reaction mixture which illustrates that expression of the gene encoding a geranylgeranyl diphosphate synthase results in production of GGPP.

The prenyltransferase activity observed was dependent upon the presence of FPP, since no counts were obtained when the pUC118/BTS1 extract was assayed in the absence of FPP (not shown). The radioactive product of this incubation co-eluted with unlabeled synthetic GGPP, indicating that it is GGPP (FIG. 6). No conversion of FPP to GGPP was seen with the pUC118 control. Both extracts also showed low levels of activity in the conversion of DMAPP to an acid-labile product. However, because the extent of conversion was the same for both samples, this activity could not be due to Bts1p (not shown).

In summary, bacterial lysates that express Bts1p were found to contain an activity that synthesizes GGPP from IPP and FPP. Therefore, BTS1 encodes a geranylgeranyl diphosphate synthase.

EXAMPLE 7

The following example shows the mechanism by which the overexpression of BTS1 (GGPP synthase) suppresses the lethality of the bet2-1 mutant.

One possibility for the BTS1 mechanism of suppression is that BTS1 suppresses by increasing the intracellular pool of GGPP, thereby compensating for a mutant GGTase-II that has a lower affinity for GGPP. To test this hypothesis, the GGTase-II activity of wild type and bet2-1 mutant extracts were measured in the presence of varying concentrations of GGPP. As a control, the activity of bet4-2 mutant extracts was also assessed. BET4 encodes the α-subunit of the GGTase-II, and extracts prepared from this mutant are devoid of GGTase-II activity.

Yeast cells were grown in YPD medium at 25° C. to late log phase. The cells were harvested, lysed with glass beads, and centrifuged at 100,000×g for 45 min. The soluble fraction was collected and assayed for GGTase-II activity. Prenylation assays were performed in a 50-μl reaction that contained 50 mM Tris-HCl (pH 7.5), 10 mM $MgCl_2$, 5 mM dithiothreitol, 25 μg of extract, 0.4 μM of recombinant Ypt1p, and varying concentrations of [$^3$H]GGPP (American Research Lab, 17,500 dpm/pmol). The reaction mixture was incubated at 30° C. for 30 min before it was terminated with 1M HCl in ethanol (1 ml) and filtered on a Whatman GF/A filter.

Figure 7:
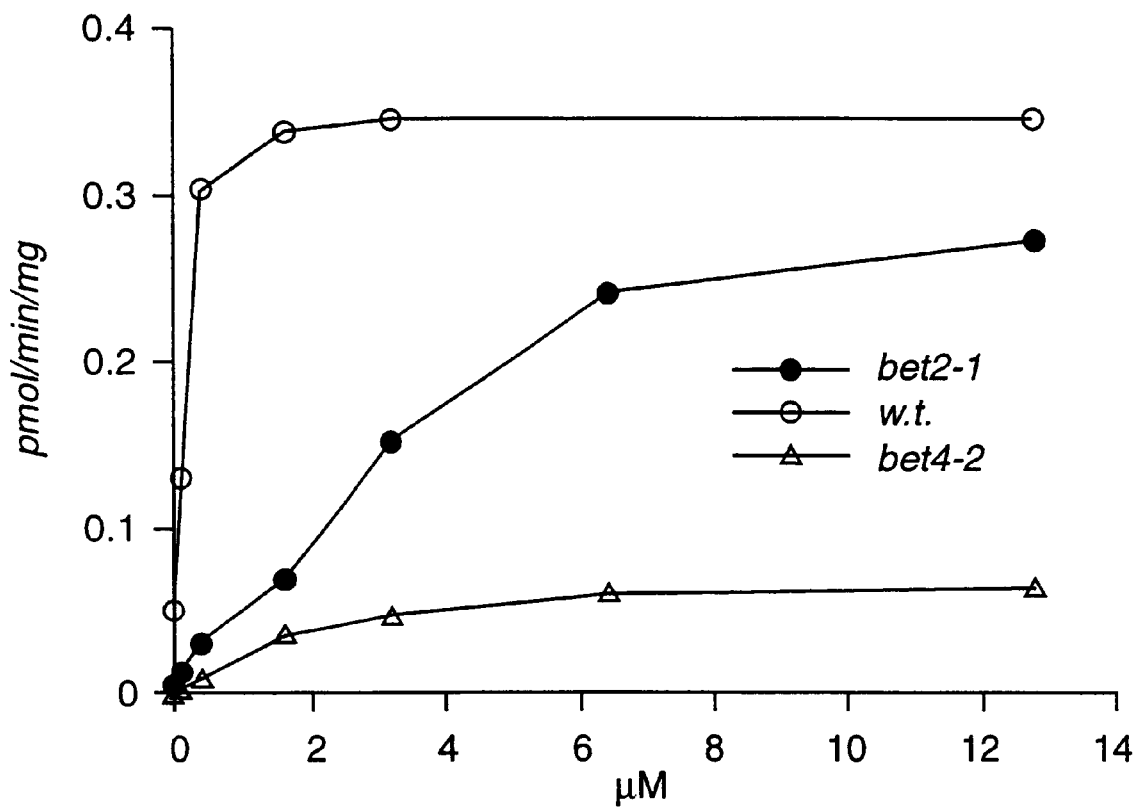
FIG. 7 shows the saturation curves of [3H]GGPP demonstrating that GGTase-II in a GGTase-II mutant has a reduced affinity for GGPP.

Unlike bet2-1, the overexpression of BTS1 does not suppress the temperature-sensitive growth defect of the bet4-2 mutant (data not shown). As shown in FIG. 7, the GGTase-II activity of the wild type extract was saturated at ~0.8 μM of GGPP. At this concentration, the activity of the bet2-1 mutant extract was approximately 5–10% of wild type. This activity was significantly enhanced when the GGPP concentration was increased beyond 2 uM, and saturation was achieved at 6 μM. In contrast, the GGTase-II activity of the bet4-2 mutant extract could not be compensated for by increasing the concentration of GGPP. The calculated $K_m$ values of GGTase-II in the bet2-1 mutant and wild type were ~3.6 and 0.4 μM, respectively. Therefore, it appears that GGTase-II in the bet2-1 mutant has a reduced affinity for GGPP, which results in a decrease in prenylation activity. By increasing the amount of GGPP that is added to the assay, prenylation activity is efficiently restored. This result provides a clear explanation for the suppression of the GGTase-II mutant, bet2-1, by GGPP synthase (BTS1).

The suppression of the bet2-1 mutant by BTS1 could be explained in several ways. The BTS1 gene product may itself have GGTase-II activity, or it could directly interact with GGTase-II to stimulate its activity. In either situation, the overexpression of BTS1 would be expected to increase GGTase-II activity. However, this was not observed by the present inventors. Alternatively, suppression may simply be a consequence of increasing the intracellular pool of GGPP. Since in vitro prenylation studies have demonstrated that mutant GGTase-II has a low affinity (increased $K_m$) for GGPP, which is compensated for by higher concentrations of GGPP, without being bound by theory, the present inventors believe that this alternate explanation is correct. According to this model, additional copies of BTS1 should result in higher intracellular concentrations of GGPP and enhanced suppression of bet2-1, thus explaining why the suppression of bet2-1 by BTS1 is gene dosage dependent.

Since BTS1 is not essential for the growth of yeast cells, it might be expected that the synthase gene may be duplicated. DNA hybridization experiments, however, argue against this possibility. Another explanation for the dispensability of BTS1 is that GGTase-II might utilize FPP as an alternate substrate. However, since GGTase-II cannot transfer FPP to Ypt1p, this possibility is also unlikely. Furthermore, extracts prepared from ΔBTS1 cells do not support the transfer of [$^3$H]FP onto Ypt1p. Thus, it is more likely that another prenyltransferase, such as hexaprenyl diphosphate synthase, might produce small amounts of GGPP as an intermediate product during the elongation of FPP to longer polyisoprenoid chains. In the ΔBTS1 strain, GGPP may be formed in this way, enabling yeast cells to survive at certain temperatures in the absence of the geranylgeranyl synthase.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:5 submitted herewith are the same.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 1005 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1005

(xi) SEQUENCE DESCRIPTION: SEQ ID NO:1:

```
ATG GAG GCC AAG ATA GAT GAG CTG ATC AAT AAT GAT CCT GTT TGG TCC        48
Met Glu Ala Lys Ile Asp Glu Leu Ile Asn Asn Asp Pro Val Trp Ser
 1               5                  10                  15

AGC CAA AAT GAA AGC TTG ATT TCA AAA CCT TAT AAT CAC ATC CTT TTG        96
Ser Gln Asn Glu Ser Leu Ile Ser Lys Pro Tyr Asn His Ile Leu Leu
             20                  25                  30

AAA CCT GGC AAG AAC TTT AGA CTA AAT TTA ATA GTT CAA ATT AAC AGA       144
Lys Pro Gly Lys Asn Phe Arg Leu Asn Leu Ile Val Gln Ile Asn Arg
         35                  40                  45

GTT ATG AAT TTG CCC AAA GAC CAG CTG GCC ATA GTT TCG CAA ATT GTT       192
Val Met Asn Leu Pro Lys Asp Gln Leu Ala Ile Val Ser Gln Ile Val
     50                  55                  60

GAG CTC TTG CAT AAT TCC AGC CTT TTA ATC GAC GAT ATA GAA GAT AAT       240
Glu Leu Leu His Asn Ser Ser Leu Leu Ile Asp Asp Ile Glu Asp Asn
 65                  70                  75                  80

GCT CCC TTG AGA AGG GGA CAG ACC ACT TCT CAC TTA ATC TTC GGT GTA       288
Ala Pro Leu Arg Arg Gly Gln Thr Thr Ser His Leu Ile Phe Gly Val
                 85                  90                  95

CCC TCC ACT ATA AAC ACC GCA AAT TAT ATG TAT TTC AGA GCC ATG CAA       336
Pro Ser Thr Ile Asn Thr Ala Asn Tyr Met Tyr Phe Arg Ala Met Gln
            100                 105                 110

CTT GTA TCG CAG CTA ACC ACA AAA GAG CCT TTG TAT CAT AAT TTG ATT       384
Leu Val Ser Gln Leu Thr Thr Lys Glu Pro Leu Tyr His Asn Leu Ile
        115                 120                 125

ACG ATT TTC AAC GAA GAA TTG ATC AAT CTA CAT AGG GGA CAA GGC TTG       432
Thr Ile Phe Asn Glu Glu Leu Ile Asn Leu His Arg Gly Gln Gly Leu
    130                 135                 140

GAT ATA TAC TGG AGA GAC TTT CTG CCT GAA ATC ATA CCT ACT CAG GAG       480
Asp Ile Tyr Trp Arg Asp Phe Leu Pro Glu Ile Ile Pro Thr Gln Glu
145                 150                 155                 160

ATG TAT TTG AAT ATG GTT ATG AAT AAA ACA GGC GGC CTT TTC AGA TTA       528
Met Tyr Leu Asn Met Val Met Asn Lys Thr Gly Gly Leu Phe Arg Leu
                165                 170                 175

ACG TTG AGA CTC ATG GAA GCG CTG TCT CCT TCA CAC CAC GGC CAT           576
Thr Leu Arg Leu Met Glu Ala Leu Ser Pro Ser His His Gly His
            180                 185                 190

TCG TTG GTT CCT TTC ATA AAT CTT CTG GGT ATT ATT TAT CAG ATT AGA       624
Ser Leu Val Pro Phe Ile Asn Leu Leu Gly Ile Ile Tyr Gln Ile Arg
        195                 200                 205

GAT GAT TAC TTG AAT TTG AAA GAT TTC CAA ATG TCC AGC GAA AAA GGC       672
Asp Asp Tyr Leu Asn Leu Lys Asp Phe Gln Met Ser Ser Glu Lys Gly
    210                 215                 220
```

```
TTT GCT GAG GAC ATT ACA GAG GGG AAG TTA TCT TTT CCC ATC GTC CAC      720
Phe Ala Glu Asp Ile Thr Glu Gly Lys Leu Ser Phe Pro Ile Val His
225                 230                 235                 240

GCC CTT AAC TTC ACT AAA ACG AAA GGT CAA ACT GAG CAA CAC AAT GAA      768
Ala Leu Asn Phe Thr Lys Thr Lys Gly Gln Thr Glu Gln His Asn Glu
            245                 250                 255

ATT CTA AGA ATT CTC CTG TTG AGG ACA AGT GAT AAA GAT ATA AAA CTA      816
Ile Leu Arg Ile Leu Leu Leu Arg Thr Ser Asp Lys Asp Ile Lys Leu
        260                 265                 270

AAG CTG ATT CAA ATA CTG GAA TTC GAC ACC AAT TCA TTG GCC TAC ACC      864
Lys Leu Ile Gln Ile Leu Glu Phe Asp Thr Asn Ser Leu Ala Tyr Thr
    275                 280                 285

AAA AAT TTT ATT AAT CAA TTA GTG AAT ATG ATA AAA AAT GAT AAT GAA      912
Lys Asn Phe Ile Asn Gln Leu Val Asn Met Ile Lys Asn Asp Asn Glu
290                 295                 300

AAT AAG TAT TTA CCT GAT TTG GCT TCG CAT TCC GAC ACC GCC ACC AAT      960
Asn Lys Tyr Leu Pro Asp Leu Ala Ser His Ser Asp Thr Ala Thr Asn
305                 310                 315                 320

TTA CAT GAC GAA TTG TTA TAT ATA ATA GAC CAC TTA TCC GAA TTG          1005
Leu His Asp Glu Leu Leu Tyr Ile Ile Asp His Leu Ser Glu Leu
                325                 330                 335

(2) INFORMATION FOR SEQ ID NO:2:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Ala Lys Ile Asp Glu Leu Ile Asn Asn Asp Pro Val Trp Ser
1               5                   10                  15

Ser Gln Asn Glu Ser Leu Ile Ser Lys Pro Tyr Asn His Ile Leu Leu
            20                  25                  30

Lys Pro Gly Lys Asn Phe Arg Leu Asn Leu Ile Val Gln Ile Asn Arg
        35                  40                  45

Val Met Asn Leu Pro Lys Asp Gln Leu Ala Ile Val Ser Gln Ile Val
    50                  55                  60

Glu Leu Leu His Asn Ser Ser Leu Leu Ile Asp Ile Glu Asp Asn
65                  70                  75                  80

Ala Pro Leu Arg Arg Gly Gln Thr Thr Ser His Leu Ile Phe Gly Val
                85                  90                  95

Pro Ser Thr Ile Asn Thr Ala Asn Tyr Met Tyr Phe Arg Ala Met Gln
            100                 105                 110

Leu Val Ser Gln Leu Thr Thr Lys Glu Pro Leu Tyr His Asn Leu Ile
        115                 120                 125

Thr Ile Phe Asn Glu Glu Leu Ile Asn Leu His Arg Gly Gln Gly Leu
    130                 135                 140

Asp Ile Tyr Trp Arg Asp Phe Leu Pro Glu Ile Ile Pro Thr Gln Glu
145                 150                 155                 160

Met Tyr Leu Asn Met Val Met Asn Lys Thr Gly Gly Leu Phe Arg Leu
                165                 170                 175

Thr Leu Arg Leu Met Glu Ala Leu Ser Pro Ser Ser His Gly His
            180                 185                 190

Ser Leu Val Pro Phe Ile Asn Leu Leu Gly Ile Ile Tyr Gln Ile Arg
        195                 200                 205

Asp Asp Tyr Leu Asn Leu Lys Asp Phe Gln Met Ser Ser Glu Lys Gly
```

```
            210                 215                 220
Phe Ala Glu Asp Ile Thr Glu Gly Lys Leu Ser Phe Pro Ile Val His
225                 230                 235                 240

Ala Leu Asn Phe Thr Lys Thr Lys Gly Gln Thr Glu Gln His Asn Glu
                245                 250                 255

Ile Leu Arg Ile Leu Leu Leu Arg Thr Ser Asp Lys Asp Ile Lys Leu
                260                 265                 270

Lys Leu Ile Gln Ile Leu Glu Phe Asp Thr Asn Ser Leu Ala Tyr Thr
            275                 280                 285

Lys Asn Phe Ile Asn Gln Leu Val Asn Met Ile Lys Asn Asp Asn Glu
290                 295                 300

Asn Lys Tyr Leu Pro Asp Leu Ala Ser His Ser Asp Thr Ala Thr Asn
305                 310                 315                 320

Leu His Asp Glu Leu Leu Tyr Ile Ile Asp His Leu Ser Glu Leu
                325                 330                 335
```

(2) INFORMATION FOR SEQ ID NO:3:

(i) SEQUENCE CHARACTERISTICS:
        (A) LENGTH: 1569 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
AATATTACAT ATAGATATAG GACAAGCCCG CATTTTCATA CTGAAAGGTA AACTTCTATT      60

ATTATAGTGG TATCCAACGT TCACCGCTTC CAGCATAGCA GAAATTACGT GTTTTTGCAT     120

ATGTTATGCT GATCATTGTA TGCTTACTAC CATTTTTCTT TGCTTCGCCT TGCCTTCTTT     180

GACGTTTTTT TGAAGCAAAA AAAAAGTCAA GACAGATGTG CTTACAAAAC CATGTAAGGC     240

TCATTTTCAA AGAAGCTACT AATAGAAAGA GAACAAAGAG TTTACGAGTC TGGAAAATCA     300

ATGGAGGCCA AGATAGATGA GCTGATCAAT AATGATCCTG TTTGGTCCAG CCAAAATGAA     360

AGCTTGATTT CAAAACCTTA TAATCACATC CTTTTGAAAC CTGGCAAGAA CTTTAGACTA     420

AATTTAATAG TTCAAATTAA CAGAGTTATG AATTTGCCCA AAGACCAGCT GGCCATAGTT     480

TCGCAAATTG TTGAGCTCTT GCATAATTCC AGCCTTTTAA TCGACGATAT AGAAGATAAT     540

GCTCCCTTGA GAAGGGGACA GACCACTTCT CACTTAATCT TCGGTGTACC CTCCACTATA     600

AACACCGCAA ATTATATGTA TTTCAGAGCC ATGCAACTTG TATCGCAGCT AACCACAAAA     660

GAGCCTTTGT ATCATAATTT GATTACGATT TTCAACGAAG AATTGATCAA TCTACATAGG     720

GGACAAGGCT TGGATATATA CTGGAGAGAC TTTCTGCCTG AAATCATACC TACTCAGGAG     780

ATGTATTTGA ATATGGTTAT GAATAAAACA GGCGGCCTTT TCAGATTAAC GTTGAGACTC     840

ATGGAAGCGC TGTCTCCTTC CTCACACCAC GGCCATTCGT TGGTTCCTTT CATAAATCTT     900

CTGGGTATTA TTTATCAGAT TAGAGATGAT TACTTGAATT TGAAAGATTT CCAAATGTCC     960

AGCGAAAAAG GCTTTGCTGA GGACATTACA GAGGGGAAGT TATCTTTTCC CATCGTCCAC    1020

GCCCTTAACT TCACTAAAAC GAAAGGTCAA ACTGAGCAAC ACAATGAAAT TCTAAGAATT    1080

CTCCTGTTGA GGACAAGTGA TAAAGATATA AAACTAAAGC TGATTCAAAT ACTGGAATTC    1140

GACACCAATT CATTGGCCTA CACCAAAAAT TTTATTAATC AATTAGTGAA TATGATAAAA    1200

AATGATAATG AAAATAAGTA TTTACCTGAT TTGGCTTCGC ATTCCGACAC CGCCACCAAT    1260

TTACATGACG AATTGTTATA TATAATAGAC CACTTATCCG AATTGTGAAA TAAATTGATC    1320
```

| | |
|---|---|
| AATCAAATTA GTGGAGGAAG ATAGTCAGAA ATAAAGCCTT CTCTCCTCCT CTTTCGCATC | 1380 |
| TATACATACG ATTTCATATA TACGTTTCAT TGCATCATCT TTTGATATAT CTCAAAAGA | 1440 |
| TCTCTTAGTT CGCAAATAGT CAAATCTTCA AATTTATAGC CTTTATATTT TTTCCACGAT | 1500 |
| TTCTGAAACT CCTTTTTATC AGCACCGTTA ATGCTAGCGG TTACTGTCAA ATCGCCGGTA | 1560 |
| AATTCGCGA | 1569 |

(2) INFORMATION FOR SEQ ID NO:4:

(i) SEQUENCE CHARACTERISTICS:
        (A) LENGTH: 1005 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

| | |
|---|---|
| TACCTCCGGT TCTATCTACT CGACTAGTTA TTACTAGGAC AAACCAGGTC GGTTTTACTT | 60 |
| TCGAACTAAA GTTTTGGAAT ATTAGTGTAG GAAAACTTTG GACCGTTCTT GAAATCTGAT | 120 |
| TTAAATTATC AAGTTTAATT GTCTCAATAC TTAAACGGGT TTCTGGTCGA CCGGTATCAA | 180 |
| AGCGTTTAAC AACTCGAGAA CGTATTAAGG TCGGAAAATT AGCTGCTATA TCTTCTATTA | 240 |
| CGAGGGAACT CTTCCCCTGT CTGGTGAAGA GTGAATTAGA AGCCACATGG GAGGTGATAT | 300 |
| TTGTGGCGTT TAATATACAT AAAGTCTCGG TACGTTGAAC ATAGCGTCGA TTGGTGTTTT | 360 |
| CTCGGAAACA TAGTATTAAA CTAATGCTAA AAGTTGCTTC TTAACTAGTT AGATGTATCC | 420 |
| CCTGTTCCGA ACCTATATAT GACCTCTCTG AAAGACGGAC TTTAGTATGG ATGAGTCCTC | 480 |
| TACATAAACT TATACCAATA CTTATTTTGT CCGCCGGAAA AGTCTAATTG CAACTCTGAG | 540 |
| TACCTTCGCG ACAGAGGAAG GAGTGTGGTG CCGGTAAGCA ACCAAGGAAA GTATTTAGAA | 600 |
| GACCCATAAT AAATAGTCTA ATCTCTACTA ATGAACTTAA ACTTTCTAAA GGTTTACAGG | 660 |
| TCGCTTTTTC CGAAACGACT CCTGTAATGT CTCCCCTTCA ATAGAAAAGG GTAGCAGGTG | 720 |
| CGGGAATTGA AGTGATTTTG CTTTCCAGTT TGACTCGTTG TGTTACTTTA AGATTCTTAA | 780 |
| GAGGACAACT CCTGTTCACT ATTTCTATAT TTTGATTTCG ACTAAGTTTA TGACCTTAAG | 840 |
| CTGTGGTTAA GTAACCGGAT GTGGTTTTTA AAATAATTAG TTAATCACTT ATACTATTTT | 900 |
| TTACTATTAC TTTTATTCAT AAATGGACTA AACCGAAGCG TAAGGCTGTG GCGGTGGTTA | 960 |
| AATGTACTGC TTAACAATAT ATATTATCTG GTGAATAGGC TTAAC | 1005 |

(2) INFORMATION FOR SEQ ID NO:5:

(i) SEQUENCE CHARACTERISTICS:
        (A) LENGTH: 1569 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

| | |
|---|---|
| TTATAATGTA TATCTATATC CTGTTCGGGC GTAAAAGTAT GACTTTCCAT TTGAAGATAA | 60 |
| TAATATCACC ATAGGTTGCA AGTGGCGAAG GTCGTATCGT CTTTAATGCA CAAAAACGTA | 120 |
| TACAATACGA CTAGTAACAT ACGAATGATG GTAAAAAGAA ACGAAGCGGA ACGGAAGAAA | 180 |
| CTGCAAAAAA ACTTCGTTTT TTTTTCAGTT CTGTCTACAC GAATGTTTTG GTACATTCCG | 240 |
| AGTAAAAGTT TCTTCGATGA TTATCTTTCT CTTGTTTCTC AAATGCTCAG ACCTTTTAGT | 300 |

-continued

```
TACCTCCGGT TCTATCTACT CGACTAGTTA TTACTAGGAC AAACCAGGTC GGTTTTACTT      360

TCGAACTAAA GTTTTGGAAT ATTAGTGTAG GAAAACTTTG GACCGTTCTT GAAATCTGAT      420

TTAAATTATC AAGTTTAATT GTCTCAATAC TTAAACGGGT TTCTGGTCGA CCGGTATCAA      480

AGCGTTTAAC AACTCGAGAA CGTATTAAGG TCGGAAAATT AGCTGCTATA TCTTCTATTA      540

CGAGGGAACT CTTCCCCTGT CTGGTGAAGA GTGAATTAGA AGCCACATGG GAGGTGATAT      600

TTGTGGCGTT TAATATACAT AAAGTCTCGG TACGTTGAAC ATAGCGTCGA TTGGTGTTTT      660

CTCGGAAACA TAGTATTAAA CTAATGCTAA AAGTTGCTTC TTAACTAGTT AGATGTATCC      720

CCTGTTCCGA ACCTATATAT GACCTCTCTG AAAGACGGAC TTTAGTATGG ATGAGTCCTC      780

TACATAAACT TATACCAATA CTTATTTTGT CCGCCGGAAA AGTCTAATTG CAACTCTGAG      840

TACCTTCGCG ACAGAGGAAG GAGTGTGGTG CCGGTAAGCA ACCAAGGAAA GTATTTAGAA      900

GACCCATAAT AAATAGTCTA ATCTCTACTA ATGAACTTAA ACTTTCTAAA GGTTTACAGG      960

TCGCTTTTTC CGAAACGACT CCTGTAATGT CTCCCCTTCA ATAGAAAAGG GTAGCAGGTG     1020

CGGGAATTGA AGTGATTTTG CTTTCCAGTT TGACTCGTTG TGTTACTTTA AGATTCTTAA     1080

GAGGACAACT CCTGTTCACT ATTTCTATAT TTTGATTTCG ACTAAGTTTA TGACCTTAAG     1140

CTGTGGTTAA GTAACCGGAT GTGGTTTTTA AAATAATTAG TTAATCACTT ATACTATTTT     1200

TTACTATTAC TTTTATTCAT AAATGGACTA AACCGAAGCG TAAGGCTGTG GCGGTGGTTA     1260

AATGTACTGC TTAACAATAT ATATTATCTG GTGAATAGGC TTAACACTTT ATTTAACTAG     1320

TTAGTTTAAT CACCTCCTTC TATCAGTCTT TATTTCGGAA GAGAGGAGGA GAAAGCGTAG     1380

ATATGTATGC TAAAGTATAT ATGCAAAGTA ACGTAGTAGA AAACTATATA GAGTTTTTCT     1440

AGAGAATCAA GCGTTTATCA GTTTAGAAGT TTAAATATCG GAAATATAAA AAAGGTGCTA     1500

AAGACTTTGA GGAAAAATAG TCGTGGCAAT TACGATCGCC AATGACAGTT TAGCGGCCAT     1560

TTAAGCGCT                                                             1569
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A recombinant nucleic acid molecule comprising a nucleic acid sequence encoding a Saccharomyces geranylgeranyl diphosphate synthase protein, wherein said nucleic acid sequence hybridizes under stringent hybridization conditions to the nucleic acid sequence of SEQ ID NO:1.

2. A recombinant nucleic acid molecule as set forth in claim 1, wherein said nucleic acid sequence encodes a Saccharomyces cerevisiae geranylgeranyl diphosphate synthase protein.

3. A recombinant nucleic acid molecule as set forth in claim 1, wherein said nucleic acid molecule comprises the nucleic acid sequence of SEQ ID NO:1.

4. The nucleic acid molecule nGGPPS$_{1005}$ having a coding strand of nucleic acid sequence SEQ ID NO:1.

5. The nucleic acid molecule nGGPPS$_{1600}$ having a coding strand of nucleic acid sequence SEQ ID NO:3.

6. A recombinant nucleic acid molecule as set forth in claim 1 operatively linked to a transcription control sequence.

7. A recombinant cell comprising a recombinant nucleic acid molecule as set forth in claim 1, said cell being capable of expressing said nucleic acid molecule.

8. A recombinant nucleic acid molecule comprising a nucleic acid sequence encoding a geranylgeranyl diphosphate synthase, wherein said nucleic acid sequence hybridizes under stringent hybridization conditions to the nucleic acid sequence of SEQ ID NO:1.

9. A recombinant nucleic acid molecule as set forth in claim 8, wherein said nucleic acid sequence encodes a GGPP synthase protein comprising the amino acid sequence of SEQ ID NO:2.

10. A recombinant nucleic acid molecule as set forth in claim 8, wherein said recombinant nucleic acid molecule encodes a geranylgeranyl diphosphate (GGPP) synthase fusion protein comprising a polypeptide encoded by said nucleic acid sequence which hybridizes under stringent hybridization conditions to the nucleic acid sequence of SEQ ID NO:1 and further comprising a nucleic acid sequence encoding a fusion polypeptide.

11. A recombinant nucleic acid molecule as set forth in claim 8, wherein said nucleic acid molecule comprises the nucleic acid sequence of SEQ ID NO:1.

12. A recombinant nucleic acid molecule as set forth in claim 8 operatively linked to a transcription control sequence.

13. A recombinant cell comprising a recombinant nucleic acid molecule as set forth in claim 7, said cell being capable of expressing said nucleic acid molecule.

14. A recombinant cell comprising a recombinant nucleic acid molecule as set forth in claim 13, wherein said cell is selected from the group consisting of bacterial cells, fungal cells, insect cells, animal cells and plant cells.

15. A recombinant cell comprising a recombinant nucleic acid molecule as set forth in claim 13, wherein said cell is a yeast cell.

16. A recombinant cell comprising a recombinant nucleic acid molecule as set forth in claim 13, wherein said cell is Saccharomyces.

17. A recombinant cell comprising a recombinant nucleic acid molecule as set forth in claim 13, wherein said cell is *Saccharomyces cerevisiae.*

18. A recombinant cell comprising a recombinant nucleic acid molecule as set forth in claim 13, wherein said cell is a bacterial cell.

19. A recombinant cell comprising a recombinant nucleic acid molecule as set forth in claim 13, wherein said cell is *Escherichia coli.*

\* \* \* \* \*

UNITED STATES PATENT AND TRADEMARK OFFICE
CERTIFICATE OF CORRECTION

PATENT NO. : 5,912,154
DATED : June 15, 1999
INVENTOR(S) : Ferro-Novick et al.

It is certified that error appears in the above-identified patent and that said Letters Patent is hereby corrected as shown below:

Column 30,
Line 63, delete "7" and insert -- 8 -- therefor.

Signed and Sealed this

Fifth Day of November, 2002

*Attest:*

*Attesting Officer*

JAMES E. ROGAN
*Director of the United States Patent and Trademark Office*